United States Patent
Aderhold

(10) Patent No.: US 8,342,743 B2
(45) Date of Patent: Jan. 1, 2013

(54) METHOD FOR TESTING A ROTOR BLADE OF A WIND POWER PLANT AND TEST DEVICE

(75) Inventor: Jochen Aderhold, Wennigsen (DE)

(73) Assignee: Fraunhofer-Gesellschaft zur Förderung der angewandten Forschung e.V., Minden (DE)

( * ) Notice: Subject to any disclaimer, the term of this patent is extended or adjusted under 35 U.S.C. 154(b) by 313 days.

(21) Appl. No.: 12/745,614

(22) PCT Filed: Nov. 24, 2008

(86) PCT No.: PCT/DE2008/001975
§ 371 (c)(1), (2), (4) Date: Jun. 1, 2010

(87) PCT Pub. No.: WO2009/071056
PCT Pub. Date: Jun. 11, 2009

(65) Prior Publication Data
US 2010/0303624 A1    Dec. 2, 2010

(30) Foreign Application Priority Data
Dec. 7, 2007   (DE) .................... 10 2007 059 502

(51) Int. Cl.
*G01N 25/72* (2006.01)

(52) U.S. Cl. .......................... 374/5; 374/137

(58) Field of Classification Search ............... 374/5, 137
See application file for complete search history.

(56) References Cited

U.S. PATENT DOCUMENTS

| | | | |
|---|---|---|---|
| 4,566,225 A * | 1/1986 | Bizot et al. ................... | 451/6 |
| 4,854,724 A | 8/1989 | Adams et al. | |
| 6,419,387 B1 | 7/2002 | Legrandjacques et al. | |
| 6,971,791 B2 * | 12/2005 | Borden et al. ................ | 374/5 |

(Continued)

FOREIGN PATENT DOCUMENTS

EP   0394932   10/1990

(Continued)

OTHER PUBLICATIONS

Meinlschmidt, P., et al., "Thermographic Inspection of Rotor Blades", NTD.Net, vol. 11, No. 11. Sep. 26, 2004, ECNDT 2006. pp. 1-9.
Bauer, A.J., "Heat-Flux thermography discovers invisible flaws", Werkstatt Online, vol. 9/2004, Sep. 2004, pp. 469-471.

*Primary Examiner* — Christopher Fulton
(74) *Attorney, Agent, or Firm* — Whitham Curtis Christifferson & Cook, PC

(57) ABSTRACT

The invention relates to a method for testing a rotor blade (13.1) of a wind power plant (1), which sweeps across a rotor blade surface to be covered during operation of the wind power plant, comprising the following steps: emitting a target light beam (20), in particular a target light beam having a power density, in a direction of the target light beam onto the rotor blade surface to be covered; detecting a possible reflection of the target light beam by a detection device at a point of incidence (16) on the rotor blade; electrically controlled emission of a measurement laser beam (21) which has a power density that is larger than the power density of the target light beam immediately after detection of the reflection at the point of incidence so that the rotor blade is heated at the point of incidence; measuring a temperature distribution at the point of incidence; and repeating the steps (a) to (d) for several points of incidence.

14 Claims, 1 Drawing Sheet

U.S. PATENT DOCUMENTS

| | | | |
|---|---|---|---|
| 7,407,325 B2 * | 8/2008 | Watanabe et al. | 374/43 |
| 7,416,330 B2 * | 8/2008 | Ito et al. | 374/127 |
| 8,029,186 B2 * | 10/2011 | Hamann et al. | 374/137 |
| 8,038,343 B2 * | 10/2011 | Hamann et al. | 374/137 |
| 8,210,741 B2 * | 7/2012 | Hamann et al. | 374/5 |
| 2006/0280222 A1 * | 12/2006 | Nikawa | 374/5 |

FOREIGN PATENT DOCUMENTS

| | | |
|---|---|---|
| WO | WO 03/069324 | 8/2003 |
| WO | WO 2006/074938 | 7/2006 |

* cited by examiner

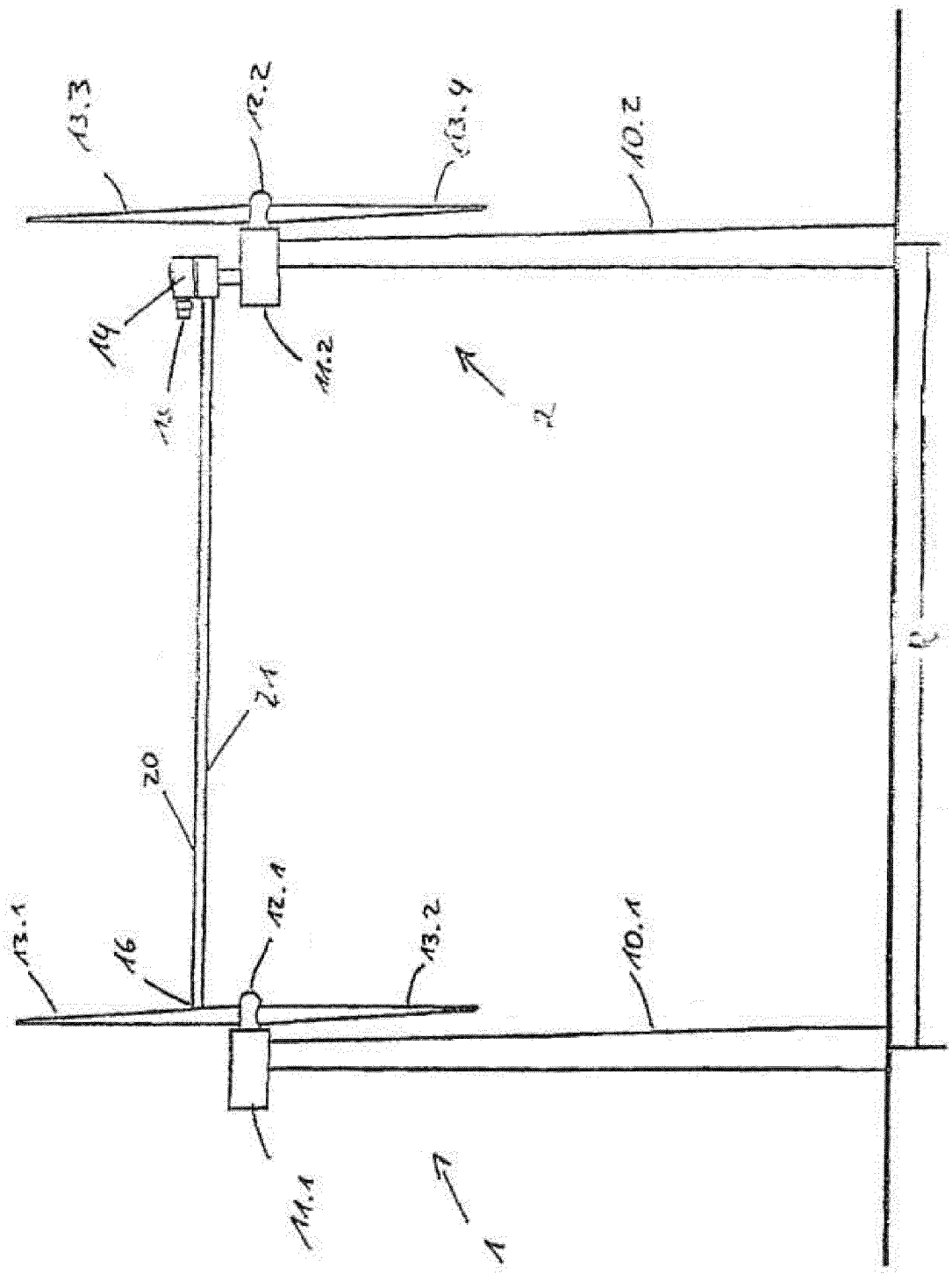

METHOD FOR TESTING A ROTOR BLADE OF A WIND POWER PLANT AND TEST DEVICE

The invention relates to a method for testing a rotor blade of a wind power installation, which covers a rotor blade coverage area during operation of the wind power installation, and to a test apparatus for carrying out the method. A second aspect of the invention relates to a test apparatus for wind power installations.

Rotor blades of wind energy installations are highly loaded components and must be regularly checked for structural faults. In the case of rotor blades mounted on a wind energy installation, a test such as this is time-consuming and costly, since they are difficult to access. This applies in particular to wind energy installations on the open sea.

U.S. Pat. No. 4,854,724 A discloses a method for non-destructive examination of weld beads and spot welds. A thermography method is used in this case, in which the spot weld to be examined or the weld bead and its surroundings is or are heated, and the temperature profile and the cool-down response are followed using a thermal imaging camera. This has the disadvantage that the method cannot be used when the object is moving. The relevant wind power installations would therefore have to be stopped in order to check the rotor blades in this way.

U.S. Pat. No. 6,419,387 B1 likewise discloses a thermography method in which small parts of the surface of a workpiece which is to be examined are heated, and the temperature profile and the cooling-down response are then observed. U.S. Pat. No. 6,419,387 B1 proposes a raster method, by means of which even relatively large-area components can be examined quickly and cost-effectively. Disadvantageously, even this is not possible during operation of a wind power installation. The same applies to WO 2006/074 938 A1, which likewise discloses a thermographic method for examination of a component for structural damage. This method can also not be carried out during operation of a wind power installation.

WO 03/069324 A1 discloses a method by means of which it is possible to examine on a thermographic basis whether adhesive which is heated during curing is present at all the intended points. The method described in WO 03/069324 A1 is used exclusively for inspection in the production process, and can therefore likewise not be used when a rotor blade is rotating during operation of the wind power installation.

The invention is based on the object of providing a method for testing a rotor blade of a wind power installation, by means of which disadvantages in the prior art can be reduced. A further aim is to provide a test apparatus which can be used to carry out the method.

The invention achieves the object by a method having the following steps:
(a) transmission of an aiming light beam, in particular of an aiming laser beam which has an aiming light beam power density, in an aiming light beam direction toward the rotor blade coverage area,
(b) detection of any reflection of the aiming light beam on an impact point on the rotor blade by a detection apparatus,
(c) directly after the detection of the reflection, electrically controlled transmission of a measurement laser beam with a measurement laser beam power density which is greater than the aiming light, beam power density, onto the impact point, such that the rotor blade is heated at the impact point,
(d) measurement of a temperature change at the impact point, and
(e) repetition of steps a) to d) for a plurality of impact points.

Before the aiming light beam is transmitted in method step a), the aiming light source is aligned with the rotor blade coverage area. The aiming light beam which is then transmitted either strikes a rotor blade and is at least partially reflected and thrown back, or passes through between two rotor blades. In order to ensure that the aiming light beam does not cause any damage in its further path in the latter case, the aiming light beam has a relatively low aiming light beam power density which, for example, is less than 1 mW/mm$^2$, preferably less than 0.1 mW/mm$^2$.

The proportion of the light of the aiming light beam which is thrown back after the aiming light beam has been reflected on a rotor blade is detected in method step b). The measurement laser beam is transmitted immediately after detection of the light of the aiming light beam thrown back from the rotor blade. Advantageously, there is less than 10 ms between the detection of the reflected light of the aiming light beam and the transmission of the measurement laser beam, particularly preferably less than 5 ms. This ensures that the test is carried out as quickly as possible. Furthermore, this short time period ensures that the aiming laser beam and the measurement lamer beam strike the rotor blade at the same point, even where the rotor blade can be caused to move slightly, for example to vibrate, for example because of the wind, even when the wind power installation is stationary.

The measurement laser beam has a measurement laser beam energy density which is higher than the aiming light beam energy density, and, for example, is more than 50 mW/mm$^2$. This ensures that the measurement laser beam strikes the rotor blade to be tested.

The measurement laser beam strikes the rotor blade to be tested. The rotor blade is therefore heated at the impact point. After a certain time period which, for example, is 10 s, the measurement laser beam is switched off. The heating of the rotor blade is thus stopped at the impact point. In the next method step, the temperature distribution on the surface of the rotor blade is measured at the impact point of the measurement laser beam and around it. Details relating to the measurement and the evaluation of the data obtained are described further below. Once the temperature distribution has been measured, method steps a) to d) are repeated at a different impact point on the rotor blade. The rotor blade can therefore be tested over a wide spatial range.

A spatial temperature distribution is advantageously measured. After the measurement laser beam has been switched off, the temperature distribution is measured on the rotor blade surface, on a position-resolved basis over an area whose diameter corresponds, for example, to five times the diameter of the measurement laser beam at the impact point.

At least one time temperature distribution is advantageously also measured. In this case, after the measurement laser beam has been switched off, the temperature distribution is measured on the surface of the rotor blade which is to be tested, on a position-resolved basis at different times.

Inhomogeneities are advantageously determined from the spatial and/or time temperature distributions, and a signal is output when a predetermined threshold value for the inhomogeneity is exceeded. After the measurement laser beam has been switched off, the energy supplied to the rotor blade surface by the measurement laser beam is dissipated into the material of the rotor blade. The temperature at the surface of the rotor blade therefore falls. The rate at which the thermal energy supplied by the measurement laser beam is dissipated, and therefore also the rate at which the temperature on the rotor blade surface falls, depends on the thermal conductivity of the rotor blade material. A rotor blade which is composed of a homogeneous material also has a homogeneous thermal conductivity. This means that the supplied heat is transported at the same speed in all directions, as a result of which the temperature likewise falls with the same characteristic at all points.

The measurement laser beam strikes the rotor blade to be tested at an impact point. At this point, the measurement laser beam ideally has a circular cross section, whose radius is, for example, 15 mm. The measurement laser beam power density is not constant within this cross section, but decreases from the center of the cross section toward the edge. This means that more energy was transmitted to the rotor blade to be tested, into the center of the impact point. The temperature distribution on the rotor blade surface is therefore also not constant within the impact point. This also falls from the center point of the impact point toward the edge. In this case, the radius of the measurement laser beam cross section is the distance from the center of the cross section in which the impacting measurement laser beam power is half the measurement laser beam power that strikes the center of the cross section.

Since the heat supplied through the measurement laser beam is transported away, and the temperature on the rotor blade surface therefore decreases at the same rate in all directions in the case of homogeneous materials, the temperature measured at one position is dependent only on the distance from the center of the impact point. The data obtained by a measurement of the spatial temperature distribution on the surface of the rotor blade with an intact rotor blade is therefore essentially rotationally symmetrical around the center point of the impact point. If, for example, one point now remains hot for considerably longer than other points at the same distance from the center of the impact point, this could be caused, for example, by an air enclosure located underneath this point. This air enclosure has a considerably lower thermal conductivity than the material surrounding it, as a result of which the thermal energy which was supplied by the measurement laser beam here cannot be transported away into the material so quickly.

A possible measured value by means of which inhomogeneities can be measured is the difference between a maximum and a minimum temperature which are measured on a ring around the center of the impact point. If this difference exceeds a previously defined threshold value, a signal is output. By way of example, this is output online or by radio to a control center or a computation center.

In order to measure the temperature change over time, a plurality measurement results of the spatial temperature distribution are carried out at different times. The time derivative of the temperature at one specific point over time is calculated therefrom. The heat flux can be deduced from this, and the thermal conductivity can be deduced from the heat flux. For a homogeneous medium, the thermal conductivity is spatially constant. The time derivative of the temperature at one position on the rotor blade over time therefore depends only on the distance of this position from the center point of the impact point. If this derivative is now considerably less at one point than at other points which are at the same distance from the center of the impact point, this indicates an air enclosure under the surface of the rotor blade. By way of example, inhomogeneities are determined by determining the time derivative of the temperature over time along a ring whose center point is the center point of the impact point. If the difference between the maximum value and the minimum value of this derivative exceeds a previously defined threshold value, a signal is output.

The temperature distribution is advantageously measured using a thermal imaging camera. This is adjusted such that it detects an area on the rotor blade surface at whose center the impact point of the measurement laser beam is located. By way of example, the area to be measured is a circle, having a diameter which corresponds to five times to ten times the diameter of the impact point.

The aiming light beam direction is advantageously changed after the temperature distribution has been measured. This ensures that a different impact point is tested in the next method run. In this case, care must be taken to ensure that both the aiming laser beam and the measurement laser beam then strike the rotor blade at a different angle. The aiming light beam in particular is in consequence reflected at a different angle, which can considerably change the intensity of the light to be detected after reflection. In order to take account of this, the sensitivity of the detection of the aiming light beam after reflection on a rotor blade is increased or decreased.

The method is advantageously carried out while the rotor blades are stationary. This results in particularly high measurement accuracy.

The measurement laser beam is advantageously at a wavelength which is beyond the human visible spectrum. This ensures that the measurement laser beam does not cause any damage, or causes minimal damage, when, for example, it does not strike a rotor blade because of a malfunction. However, a hazard can occur even when testing points on the rotor blade surface which the measurement laser beam does not strike at right angles. In this case, as in the case of the aiming light beam, a proportion of the incident light is reflected. Since the measurement laser beam has a high measurement laser beam power density, as described above, this results in a considerable hazard, which can be minimized by optimum choice of the wavelength of the measurement laser beam.

The rotor blade to be tested is preferably attached to a hub, and the aiming light beam is transmitted to impact points at different radial distances from the hub. This ensures that the rotor blade to be tested is tested comprehensively. As already described, the sensitivity of the apparatus used to detect the reflected light of the aiming light beam can be matched to a possibly different impact angle, and therefore reflection angle, of the light.

The measurement laser beam and the aiming light beam are preferably transmitted on a common beam path. This ensures that a transmitted measurement laser beam strikes a rotor blade since, obviously, the aiming light beam has also been reflected.

The aiming light beam and the measurement laser beam are preferably transmitted from a measurement apparatus which is mounted on a second wind power installation. In this case, at least in the relatively close vicinity of the hub to which the rotor blade to be tested is attached, the aiming light beam strikes the rotor blade essentially at right angles, as a result of which the maximum intensity of the aiming light beam can be reflected. Furthermore, the process ensures, in particular, that the measurement laser beam cannot be located at eye level of any passers-by or animals, where it could cause damage.

A test apparatus according to the invention for wind power installations comprises an aiming light source which has an aiming light beam power density, a detection apparatus, which is designed to detect any reflection of the aiming light beam on a rotor blade of the wind power installation, a measurement laser, which has a measurement laser power density which is greater than the aiming light beam power density, and is designed to output a measurement laser beam in a measurement laser beam direction, and a temperature measurement apparatus for measuring the temperature distribution at the impact point, as well as an electrical controller, which is connected to the aiming light source, to the detection apparatus, to the measurement laser and to the temperature measurement apparatus, and is designed for carrying out one of the methods mentioned above.

In particular, diode lasers and solid-state lasers are suitable for use as aiming and measurement lasers. However, other laser types can also be used. The aiming light beam power density is, for example, less than 1 mW/mm$^2$, advantageously less than 0.1 mW/mm$^2$. In contrast, the measurement laser beam has a measurement laser beam power density which, for example, is 50 mW/mm$^2$. The electrical controller ensures that the method can be carried out automatically. A preset routine which scans the entire surface of the rotor blades by skilful choice of the impact points can be implemented easily, thus considerably reducing man hours and therefore the costs involved.

The aiming light source can advantageously be adjusted in the aiming light beam direction, and the measurement laser can be adjusted in the measurement laser beam direction, in a motorized manner. This allows the direction to be adjusted considerably more accurately than if the laser had to be adjusted by hand and, furthermore, this improves the reproducibility. For example, it is easily and precisely possible to once again set a point on a rotor blade at which the detected data is subject to errors of for which the detected data needs to be checked.

In a wind farm with two wind power installations, one of the described test apparatuses is advantageously mounted on at least one of the wind power installations, and these apparatuses are designed to carry out a method as described above. This is particularly advantageous for wind farms on the high seas since they can be accessed only with difficulty, as a result of which it is complex and costly to test the rotor blades of these wind power installations. Furthermore, the rotor blades of wind power installations on the high seas have to be checked considerably more frequently since they are subject to wear considerably more quickly because of more extreme weather conditions and the continuous influence of salt.

One exemplary embodiment of the invention will be described in more detail in the following text with reference to a drawing, in which:

FIG. 1 shows two wind energy installations, one of which is equipped with a test apparatus according to the invention, for carrying out a method according to the invention.

FIG. 1 shows a first wind power installation 1 and a second wind power installation 2, having a respective tower 10.1 and 10.2, and a respective pod 11.1 and 11.2. The pods 11.1 and 11.2 each have a hub 12.1 and 12.2, about which the rotor blades 13.1, 13.2, 13.3 and 13.4 attached thereto rotate. The two wind power installations 1 and 2 are separated by a distance R. The distance R is generally between 200 and 900 meters. A test apparatus 14 according to the invention is mounted on the pod 11.2 of the second wind power installation 2 and has an aiming laser, a detection apparatus, an aiming laser and a temperature measurement apparatus 15. FIG. 1 shows only the temperature measurement apparatus 15 of these components of the test apparatus 14.

At the start of the method for testing the rotor blade 13.1 for structural faults, the test apparatus 14 uses the aiming laser contained in it to emit an aiming laser beam 20 in the direction of the area covered by the rotor blades 13.1 and 13.2 of the wind power installation 1. The aiming laser beam in this case strikes the impact area 16 on the rotor blade 13.1 of the wind power installation 1, where at least a portion of the light is reflected, and is thrown back in the direction of the test apparatus 14 on the pod 11.2 of the wind power installation 2. This proportion of the aiming laser beam 14 that is thrown back is detected by the detection apparatus contained in the test apparatus 14. For this purpose, it is not necessary to transmit a laser beam at the start, and in principle any method is suitable which allows the position of the rotor blade to be measured to be found. The use of the combination of an aiming laser beam 20 and a measurement laser beam 21, which are preferably transmitted on one beam path, ensures greater accuracy and reproducibility, however. If the detection apparatus contained in the test apparatus 14 has found a reflection of the aiming laser beam 20 on the impact area 16 on the rotor blade 13.1, a measurement laser beam 21 is emitted. FIG. 1 shows the aiming laser beam 20 and the measurement laser beam 21 slightly offset. This is possible, but they are advantageously transmitted on one beam path.

The measurement laser beam 21 strikes the rotor blade 13.1 at the impact point 16. As a result of the high power density of the measurement laser beam 21, the temperature of the rotor blade 13.1 at the impact point 16 is increased, and the heat created there is dissipated into the material of the rotor blade 13.1. The rate at which this happens and the spatial extent which is reached depend on the thermal conductivity of the material of the rotor blade 13.1. This is changed by structural faults, for example cracks or air enclosures, thus resulting in a different temperature profile being found when the impact point has structural faults. The temperature distribution at the impact point 16 on the rotor blade 13.1 is measured via the temperature measurement apparatus 15 which, for example, may be a thermal imaging camera which is integrated in the test apparatus 14. In this case, a spectral distribution of the heat energy and the time profile of the heat transport are measured. Inhomogeneities and structural faults can be discovered from the comparison of the data determined in this way with the known data for an intact rotor blade.

Since the method can be carried out over a relatively long distance R, a suitable test apparatus can also be mounted on the ground, or, for example, in a mobile form in a car. This allows the method to be used flexibly, and there is no need to obtain a specific test apparatus for each wind power installation, thus considerably reducing the costs of the maintenance method.

LIST OF REFERENCE SYMBOLS

1 First wind power installation
2 Second wind power installation
10 Tower of a wind power installation
11 Pod
12 Hub
13 Rotor blade
14 Test apparatus
15 Temperature measurement apparatus
16 Impact area
20 Aiming laser beam
21 Measurement laser beam

The invention claimed is:

1. A method for testing a rotor blade of a wind, power installation, which covers a rotor blade coverage area during operation of the wind power installation, having the following steps:
(a) transmission of an aiming light beam, in particular of an aiming light beam which has an aiming light beam power density, in an aiming light beam direction at the rotor blade coverage area,
(b) detection of any reflection of the aiming light, beam on an impact point on the rotor blade by a detection apparatus, (c) directly after the detection of the reflection, electrically controlled transmission of a measurement later beam with a measurement laser beam power density which is greater than the aiming light beam power density, at the impact point, such that the rotor blade is heated at the impact point, (d) measurement of a temperature distribution at the impact point, and (e) repetition of steps (a) to (d) for a plurality of impact points.

2. The method as claimed in claim 1, characterized in that a spatial temperature distribution is measured.

3. The method as claimed in claim 2, characterized in that the temperature distribution is measured using a thermal imaging camera.

4. The method as claimed in claim 2, characterized by the following steps:

determination of inhomogeneities from the spatial and/or time temperature distribution, and outputting of a signal when a predetermined threshold value for at least one of the inhomogeneities is exceeded.

5. The method as claimed in claim 1, characterized in that a temperature distribution is measured at least two different times.

6. The method as claimed in claim 1, characterized by the following step:

after the measurement of the temperature distribution, variation of the aiming light beam direction.

7. The method as claimed in claim 1, characterized in that the method is carried out while the rotor blades are stationary.

8. The method as claimed in claim 1, characterized that the measurement laser beam is at a wavelength which is beyond the human visible spectrum.

9. The method as claimed in claim 1, characterized in that the rotor blade is attached to a hub, and the aiming light beam is transmitted to impact points at different radial distances from the hub.

10. The method as claimed in claim 1, characterized in that the measurement laser beam and the aiming light beam are transmitted on a common beam path.

11. The method as claimed in claim 1, characterized in that the aiming light beam and the measurement laser beam are transmitted from a measurement apparatus which is mounted on a second wind power installation.

12. A test apparatus for wind power installations comprising:

(a) an aiming light source which has an aiming light beam power density, (b) a detection apparatus, which is designed to detect any reflection of the aiming light beam at an impact point on a rotor blade of the wind power installation, (c) a measurement laser, which has a measurement laser power density which is greater than the aiming light beam power density, and is designed to output a measurement, laser beam in a measurement laser beam direction, (d) a temperature measurement apparatus for measuring a temperature distribution at the impact point, and (e) an electrical controller, which is connected to the aiming light source, to the detection apparatus, to the measurement laser and to the temperature measurement apparatus.

13. The test apparatus as claimed in claim 12, characterized in that the aiming light beam direction of the aiming light beam can be adjusted, and the measurement laser beam direction of the measurement laser can be adjusted, in a motorized manner.

14. A wind farm having at least two wind power installations, wherein a test apparatus is mounted on one of said at least two wind power installations, said test apparatus comprising:

(a) an aiming light source which has an aiming light beam power density, (b) a detection apparatus, which is designed to detect any reflection of the aiming light beam at an impact point on a rotor blade of the wind power installation, (c) a measurement laser, which has a measurement laser power density which is greater than the aiming light beam power density, and is designed to output a measurement laser beam in a measurement laser beam direction, (d) a temperature measurement apparatus for measuring a temperature distribution at the impact point, and (e) an electrical controller, which is connected to the aiming light source, to the detection apparatus, to the measurement laser and to the temperature measurement apparatus, wherein said test apparatus carries out a method for testing a rotor blade of a wind power installation which covers a rotor blade coverage area during operation of the wind power installation on a rotor blade of another wind power installation of said at least two wind power installations, which includes the following steps:

(a) transmission of an aiming light beam, in particular of an aiming light beam which has an aiming light beam power density, in an aiming light beam direction at the rotor blade coverage area, (b) detection of any reflection of the aiming light beam on an impact point on the rotor blade by a detection apparatus, (c) directly after the detection of the reflection, electrically controlled transmission of a measurement laser beam with a measurement laser beam power density which is greater than the aiming light beam power density, at the impact point, such that the rotor blade is heated at the impact point, (d) measurement of a temperature distribution at the impact point, and (e) repetition of steps (a) to (d) for a plurality of impact points.

* * * * *